US010792192B2

(12) United States Patent
Tout et al.

(10) Patent No.: US 10,792,192 B2
(45) Date of Patent: *Oct. 6, 2020

(54) MEDICAL DRESSINGS, SYSTEMS, AND METHODS EMPLOYING SEALANTS

(71) Applicant: KCI Licensing, Inc., San Antonio, TX (US)

(72) Inventors: Aidan Marcus Tout, Alderbury (GB); Timothy Mark Robinson, Shillingstone (GB)

(73) Assignee: KCI Licensing, Inc., San Antonio, TX (US)

(*) Notice: Subject to any disclaimer, the term of this patent is extended or adjusted under 35 U.S.C. 154(b) by 443 days.

This patent is subject to a terminal disclaimer.

(21) Appl. No.: 15/782,075

(22) Filed: Oct. 12, 2017

(65) Prior Publication Data

US 2018/0028366 A1 Feb. 1, 2018

Related U.S. Application Data

(60) Continuation of application No. 14/139,518, filed on Dec. 23, 2013, now Pat. No. 9,814,627, which is a (Continued)

(51) Int. Cl.
*A61F 13/00* (2006.01)
*A61F 13/02* (2006.01)
(Continued)

(52) U.S. Cl.
CPC .... *A61F 13/0216* (2013.01); *A61F 13/00068* (2013.01); *A61F 13/0253* (2013.01);
(Continued)

(58) Field of Classification Search
CPC ............ A61F 13/00068; A61F 13/0216; A61F 13/0253; A61M 1/0084; A61M 1/0088
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Benjamin J Klein

(57) ABSTRACT

According to an illustrative embodiment, a system for treating a wound at a tissue site of a patient comprising a reduced-pressure source to supply reduced pressure, a drape adhering to the tissue site to cover the wound where possible leak passages between the drape and the tissue site may occur, and a seal disposed between the drape and the tissue site, is disclosed. The seal is adapted to react with a fluid to form a sealant substantially filling the passages in response to air leaking through the passages from outside the drape when reduced pressure is applied to the wound. According to another illustrative embodiment, a method for sealing a drape to a tissue site for treating a wound at the tissue site comprising applying the drape to cover the tissue site whereby passages are formed between the drape and the tissue site, positioning a seal between the drape and the tissue site wherein the seal is adapted to react with a fluid to form a sealant for substantially filling the passages, is also disclosed.

34 Claims, 4 Drawing Sheets

Related U.S. Application Data division of application No. 12/870,535, filed on Aug. 27, 2010, now abandoned.

(60) Provisional application No. 61/242,488, filed on Sep. 15, 2009.

(51) Int. Cl.
*A61L 15/58* (2006.01)
*A61M 1/00* (2006.01)

(52) U.S. Cl.
CPC ........... *A61L 15/58* (2013.01); *A61M 1/0088* (2013.01); *A61M 1/0084* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 9,814,627 B2* | 11/2017 | Tout ................. A61F 13/00068 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |

(56) References Cited

FOREIGN PATENT DOCUMENTS

| WO | 97/18007 A1 | 5/1997 |
|---|---|---|
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

MEDICAL DRESSINGS, SYSTEMS, AND METHODS EMPLOYING SEALANTS

RELATED APPLICATION

This application is a continuation of U.S. patent application Ser. No. 14/139,518, entitled "Medical Dressings, Systems, And Methods Employing Sealants," filed December is a divisional of U.S. patent application Ser. No. 12/870,535, entitled "Medical Dressings, Systems, And Methods Employing Sealants," filed Aug. 27, 2010, which claims the benefit, under 35 USC § 119(e), of the filing of U.S. Provisional Patent Application Ser. No. 61/242,488, entitled "System and Method for Sealing a Wound," filed Sep. 15, 2009. Both applications are incorporated herein by reference for all purposes.

BACKGROUND

The present invention relates generally to medical treatment systems, and more particularly, medical dressings, systems, and methods employing sealants.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Unless otherwise indicated, as used herein, "or" does not require mutual exclusivity.

SUMMARY

According to an illustrative embodiment, a system for treating a wound at a tissue site of a patient comprising a reduced-pressure source to supply reduced pressure, a drape adhering to the tissue site to cover the wound where possible leak passages between the drape and tissue site may occur, and a seal disposed between the drape and the tissue site, is disclosed. The seal is adapted to react with a fluid to form a sealant substantially filling the passages in response to air leaking through the passages from outside the drape when reduced pressure is applied to the wound.

According to another illustrative embodiment, an apparatus includes a seal having a first side and a second, tissue-facing side. The seal is adapted for placement adjacent the tissue site and is operable to expand in a presence of a fluid to form a substantially sealed space at the tissue site. The apparatus also includes a drape for covering the sealant and further forming the substantially sealed space.

According to another illustrative embodiment, a method for sealing a drape to a tissue site for treating a wound at the tissue site comprising applying the drape to cover the tissue site whereby passages are formed between the drape and the tissue site, positioning a seal between the drape and the tissue site wherein the seal is adapted to react with a fluid to form a sealant for substantially filling the passages, is also disclosed.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein includes, without limitation, a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location. The tissue may be that of any mammal, such as a mouse, rat, rabbit, cat, dog, or primate, including humans, that are being treated as patients. Also, the wound at the tissue site may be due to a variety of causes, including trauma, surgery, degeneration, and other causes.

Figure 1:
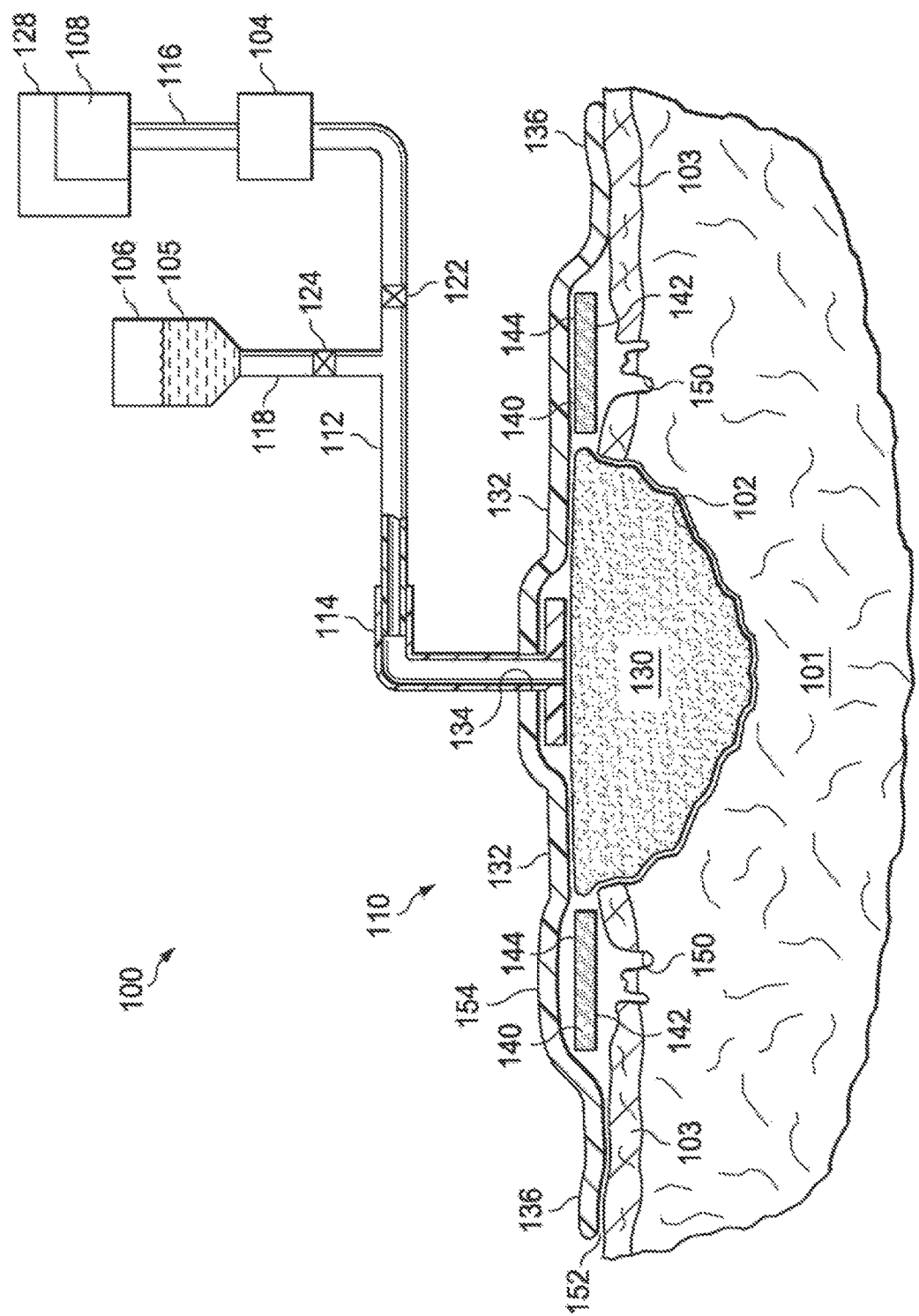
FIG. 1 is a schematic, cross-sectional view of a reduced-pressure treatment system including dressing that utilizes a sealant according to one illustrative embodiment.
Figure 2:
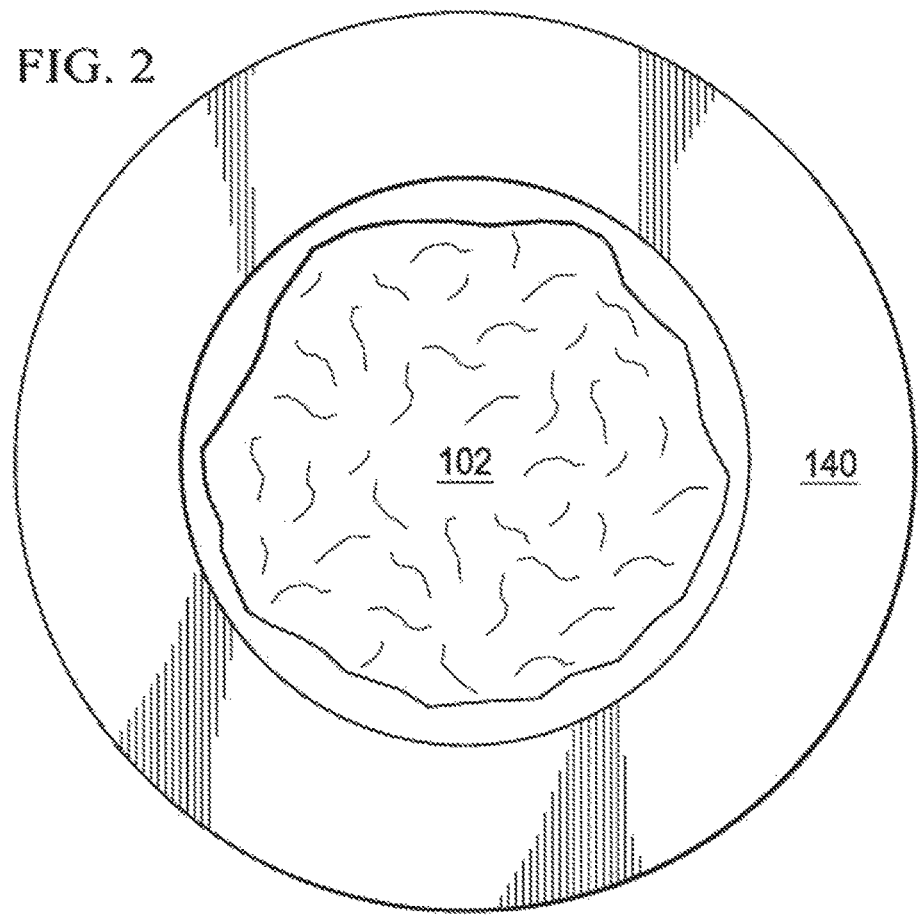
FIG. 2 is a schematic, plan view of the sealant and the wound shown in the embodiment of FIG. 1.

Referring to FIGS. 1 and 2, a reduced pressure treatment system 100 for applying a reduced pressure to a tissue site 101 of a patient according to an illustrative embodiment where the tissue site 101 includes a wound 102 surrounded by healthy tissue including, without limitation, an epidermis 103 of such tissue. The system 100 comprises a canister 104 having a filter (not shown) contained within the canister 104 and a fluid supply 106 for delivering a fluid 105 to the tissue site 101. The canister 104 is positioned in fluid communication with a reduced pressure source 108 and a reduced pressure dressing 110 that is positioned at the tissue site 101. The reduced pressure dressing 110 is fluidly connected to the canister 104 by a conduit 112. The conduit 112 may fluidly communicate with the reduced pressure dressing 110 through a tubing adapter 114. A second conduit 116 fluidly connects the canister 104 with the reduced pressure source 108.

The canister 104 may be a fluid reservoir, or collection member, to filter or hold exudates and other fluids removed from the tissue site 101. In one embodiment, the canister 104 and the reduced pressure source 108 are integrated into a single housing structure. The fluid supply 106 is fluidly connected to the reduced pressure dressing 110 by a third conduit 118 that may be connected directly to the reduced pressure dressing 110 (not shown) or indirectly via the conduit 112 which requires valves 122 and 124 for controlling the delivery of reduced pressure from the reduced pressure source 108 and/or the fluid 105 from the fluid supply 106, respectively. The fluid 105 may be any gas or liquid, and may contain growth factors, healing factors, or other substances to treat the wound 102 at the tissue site 101. For example, the fluid 105 may be air, water, saline, or dye saline.

In the embodiment illustrated in FIG. 1, the reduced pressure source 108 is an electrically-driven vacuum pump. In another implementation, the reduced pressure source 108 may instead be a manually-actuated or manually-charged pump that does not require electrical power. The reduced pressure source 108 instead may be any other type of reduced pressure pump, or alternatively a wall suction port such as those available in hospitals and other medical facilities. The reduced pressure source 108 may be housed within or used in conjunction with a reduced pressure treatment unit 128, which may also contain sensors, processing units, alarm indicators, memory, databases, software, display unites, and user interfaces that further facilitate the application of reduced pressure treatment to the tissue site 101. In one example, a sensor or switch (not shown) may be disposed at or near the reduced pressure source 108 to determine a source pressure generated by the reduced pressure source 108. The sensor may communicate with a processing unit that monitors and controls the reduced pressure that is delivered by the reduced pressure source 108.

The reduced pressure dressing 110 includes a distribution manifold 130 adapted to be positioned at the tissue site 101, and a drape 132 that covers the distribution manifold 130 to maintain reduced pressure beneath the drape 132 at the tissue site 101. The drape 132 includes an aperture 134 through which the tubing adapter 114 extends to provide fluid communication between the conduit 112 and the distribution manifold 130. The drape 132 further includes a periphery portion 136 that may extend beyond a perimeter of the tissue site 101 and may include an adhesive or bonding agent (not shown) to secure the drape 132 to tissue adjacent the tissue site 101. In one embodiment, the adhesive disposed on the drape 132 may be used to provide a seal between the epidermis 103 and the drape 132 to prevent leakage of reduced pressure from the tissue site 101. In another embodiment, a seal layer (not shown) such as, for example, a hydrogel or other material may be disposed between the drape 132 and the epidermis 103 to augment or substitute for the sealing properties of the adhesive.

The distribution manifold 130 of the reduced pressure dressing 110 is adapted to contact the tissue site 101. The distribution manifold 130 may be partially or fully in contact with the tissue site 101 being treated by the reduced pressure dressing 110. When the distribution manifold 130 is in contact with the wound 102 at the tissue site 101, the distribution manifold 130 may partially or fully fill the wound 102. The distribution manifold 130 may be any size, shape, or thickness depending on a variety of factors, such as the type of treatment being implemented or the nature and size of the tissue site 101 or the wound 102. For example, the size and shape of the distribution manifold 130 may be customized by a user to cover a particular portion of the tissue site 101, or to fill or partially fill the tissue site 101 or the wound 102. The distribution manifold 130 may have, for example, a square shape, or may be shaped as a circle, oval, polygon, an irregular shape, or any other shape. The distribution manifold 130 may further promote granulation at the tissue site 101 when a reduced pressure is applied through the reduced pressure dressing 110. For example, any or all of the surfaces of the distribution manifold 130 may have an uneven, coarse, or jagged profile that causes microstrains and stresses at the tissue site 101 when reduced pressure is applied through the distribution manifold 130. These microstrains and stresses have been shown to increase new tissue growth.

In one illustrative embodiment, the distribution manifold 130 is a foam material that distributes reduced pressure to the tissue site 101 when the distribution manifold 130 is in contact with or near the tissue site 101. The foam material may be either hydrophobic or hydrophilic. In one non-limiting example, the distribution manifold 130 is an open-cell, reticulated polyurethane foam such as GranuFoam® dressing available from Kinetic Concepts, Inc. of San Antonio, Tex. In the example in which the distribution manifold 130 is made from a hydrophilic material, the distribution manifold 130 also functions to wick fluid away from the tissue site 101, while continuing to provide reduced pressure to the tissue site 101 as a manifold. The wicking properties of the distribution manifold 130 draw fluid away from the tissue site 101 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In one embodiment, the distribution manifold 130 may be constructed from bioresorbable materials that do not have to be removed from a patient's body following use of the reduced pressure dressing 110. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The distribution manifold 130 may further serve as a scaffold for new cell-growth, or a scaffold material may be used in conjunction with the distribution manifold 130 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 132 may be any material that provides a pneumatic or fluid seal. The drape 132 may, for example, be an impermeable or semi-permeable, elastomeric material. "Elastomeric" means having the properties of an elastomer, and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of drape materials include a silicone drape, 3M Tegaderm® drape, acrylic drape such as one available from Avery Dennison, or an incise drape.

The reduced pressure dressing 110 further includes a seal 140 that is generally annular in shape and disposed between the tissue site 101 and the drape 132 thereby having a tissue-facing side 142 and a drape-facing side 144 when positioned on the tissue site 101. The drape 132 covers the seal 140 such that the periphery portion 136 of the drape 132 extends beyond the seal 140 so that the adhesive portion of the drape 132 adheres to the tissue surrounding the wound 102 at the tissue site 101. The seal 140 is substantially solid in form and substantially surrounds the wound 102 so that the tissue-facing side 142 is positioned adjacent the epidermis 103 of the tissue site 101. Even though the periphery portion 136 of the drape 132 functions as an adhesive with some sealing capability as described above, the epidermis 103 may have recesses and cracks or other discontinuities on the surface, i.e., epidermal discontinuities 150, extending beyond the periphery portion 136. These epidermal discontinuities 150 form passages 152 through which air from outside the reduced pressure dressing 110 ("external air") may leak into the tissue site 101 when reduced pressure is delivered to the distribution manifold 130. Additionally, when the drape 132 is positioned on the tissue site 101, folds or buckles in the drape 132, i.e., drape discontinuities 154, may also form the passages 152 through which external air may leak into the tissue site 101 when reduced pressure is delivered to the distribution manifold 130.

Figure 3:
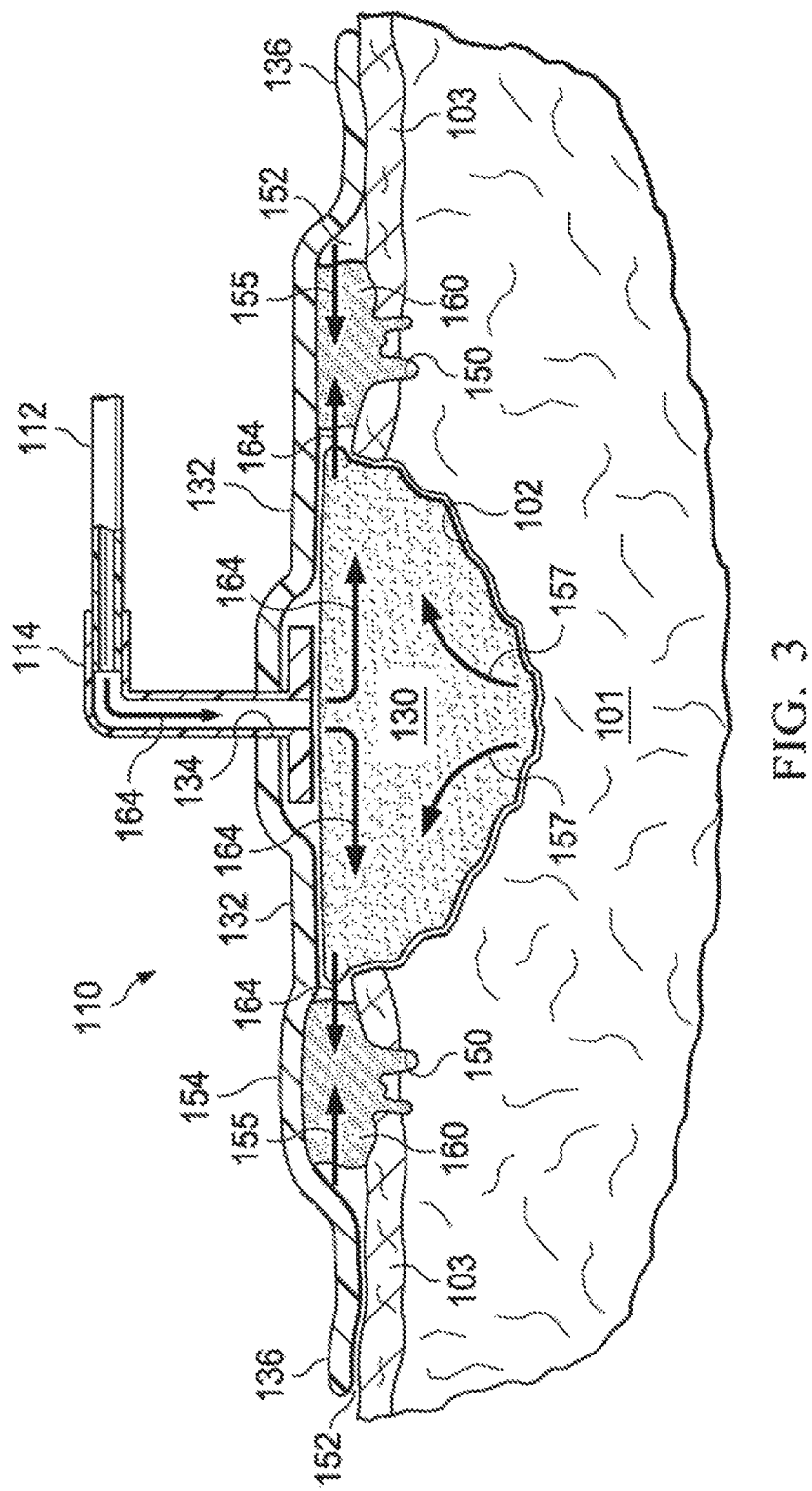
FIG. 3 is a schematic, cross-sectional view of the dressing and the sealant shown in FIG. 1 after the sealant has transformed to a gelatinous or liquid state.

Referring to FIGS. 1 and 3, the seal 140 is initially solid in form that is made from material adapted to react with fluid such as, for example, the flow of external air as indicated by arrows 155. This reaction transforms the seal 140 from solid phase to either liquid or gel which flows or expands to fill the passages 152 created by the epidermal discontinuities 150 and/or the drape discontinuities 154. Consequently, the transformed seal 140 forms a sealant 160 that fills the passages 152 and prevents the external air from leaking into the tissue site 101 when reduced pressure is delivered to the distribution manifold 130. The sealant 160 substantially blocks the passages 152 to prevent the external air from being drawn into the wound 102 by the reduced pressure, thereby maintaining the level of reduced pressure being delivered by the distribution manifold 130 to the tissue site 101.

The seal 140 may be fabricated from a material containing isocyanate that reacts with water vapor content of the external air to create carbon dioxide gas within the material causing the material to expand and fill the passages 152 forming the sealant 160 that plugs the passages 152 created by the epidermal discontinuities 150 and the drape discontinuities 154. Water-sensitive polymers may also be used to form the seal 140. For example, the seal 140 may be formed from an uncrosslinked water-sensitive polymer to liquify when exposed to moisture. The seal 140 may also be formed from a crosslinked water-sensitive polymer to swell when exposed to moisture. Water-sensitive polymers include polyacrylates, polyvinylpyrrolidone, polyvinyl alcohol, alginates, and carboxymethyl cellulose. In another example, the seal 140 may be formed from water-sensitive materials that liberate gases such as metal hydrides and carbides. Further, hygroscopic materials, such as anhydrides, may be used to form the seal 140 some of which may also increase in volume as moisture is absorbed. The transformation of a water-sensitive seal 140 to form the sealant 160 may be initiated or accelerated by first using a sponge or other application device to wet the surfaces of the seal 140 with water. Further transformation results when the water vapor content of the external air reacts with the water-sensitive material being utilized for the seal 140.

In another embodiment, the fluid supply 106 may provide the fluid 105 to the tissue site 101 via the distribution manifold 130 as described above and further indicated by arrows 164 wherein the fluid 105 includes an agent that facilitates the transformation of the seal 140 into the sealant 160 when exposed to the leakage of external air that comes in contact with the seal 140. In another embodiment, the fluid supply 106 may provide the fluid 105 to the tissue site 101 via the distribution manifold 130 as described above and further indicated by the arrows 164 wherein the fluid 105 includes an agent that causes the transformation of the seal 140 into the sealant 160 without being exposed to the leakage of external air that comes in contact with the seal 140. For example, solvents may be introduced as solutions that cause the seal 140 to liquefy or swell. As described above, the transformation of a water-sensitive seal 140 to form the sealant 160 may be initiated or accelerated by first using a sponge or other application device to wet the surfaces of the seal 140 with either water or the solvent.

Examples of solvents that may be used include alcohols, glycols, polyethylene glycols, and glycerine that react with a seal 140 that is fabricated from materials such as modified polyurethanes, acrylics, and acetates. Other solvents, incompatible with water, may also be used and introduced as emulsions or dispersions that are absorbed by the seal 140 which liquefies or swells as a result of the reaction. Examples of these water-incompatible solvents include esters, phthalates, trimellitates, citrates, and vegetable oils. The seal 140 may also be formed from polyurethane that contains an active substance that expands upon contact with the fluid 105. The polyurethane may also function as an adhesive so that the sealant 160 adheres more tightly to the drape 132 and the patient's epidermis 103.

In another embodiment, the seal 140 may also include isocyanate, tartaric acid and sodium bicarbonate, super absorbent fiber that expands when exposed to a fluid, or water-absorbing polymers that swell when exposed to a fluid. In the example in which the seal 140 is formed from a fiber, the fiber may form a mesh such that the fibers are oriented along at least two directions and intersect with one another. In one embodiment, the expansion of the seal 140 may be caused by the formation of bubbles within the seal 140 after it transforms into the sealant 160. These bubbles may be caused by the release of carbon dioxide upon contact between the seal 140 and the fluid 105. The specific material used for the seal 140 may depend upon the manner in which the expansion of the seal 140 is activated. Also, the shape of the seal 140 can vary depending on the manner in which the seal 140 is used or applied.

The expansion of the seal 140 can be activated using any of a variety of mechanisms depending on the embodiment employed, and several non-limiting examples follow. In one example, as discussed above, the seal 140 expands in the presence of the fluid 105 delivered from the fluid supply 106 via the distribution manifold 130 as indicated by the arrows 164 in FIG. 3. The fluid 105 flows through the distribution manifold 130 and contacts the seal 140 causing it to expand to fill the passages 152 created by the epidermal discontinuities 150 and the drape discontinuities 154 as described above. The fluid 105 may continue to be supplied to the sealant 160 after the expansion of the seal 140 to provide therapy to the wound 102.

The fluid used to activate and expand the seal 140 may originate from sources other than the fluid supply 106. In one embodiment, the fluid supplied to the seal 140 may be exudate from the wound 102. In this example, the exudate flows to the seal 140 as indicated by exudate flow arrows 157. In another example, fluid may be supplied to the seal 140 by pre-applying the fluid to the tissue site 101 with a sponge or other application device and, more specifically, the surface layer of the epidermis 103, before applying the reduced pressure dressing 110 to the tissue site 101. This pre-applied fluid may be a gel or liquid sufficient to activate the expansion of the seal 140. In yet another example, a fluid may be applied to the seal 140 from under the periphery portion 136 of the drape 132 after the reduced pressure dressing 110 has been applied to the tissue site 101. In this example the fluid may be sprayed, injected, or otherwise applied onto or into the seal 140 by a care giver, including the patient. Although the care giver may desire to expose all or a substantial portion of the seal 140 to the fluid, the care giver may also apply the fluid to targeted regions of the seal 140 based on an assessment of the areas in the reduced pressure dressing 110 where the passages 152 are detected. Using this technique, a care giver may determine the areas at which a fluid lead exists in the reduced pressure dressing 110, and apply the fluid to those portions of the seal 140 that are adjacent the passages 152.

In another example of a mechanism by which the seal 140 may be exposed to a fluid, reduced pressure may be applied to the distribution manifold 130 so that the external air is drawn to the seal 140 from the outside of the reduced pressure dressing 110 through the passages 152 as described above and as indicated by the arrows 155. When contacting the seal 140, the vapor or humidity within the air reacts with the seal 140 as described above. The seal 140 may be formed from material that reacts with the air or component thereof. For example, the seal 140 may react with oxygen, carbon dioxide, or other component of the gas to cause the expansion of the seal 140. In another embodiment, the seal 140 may be formed from material that reacts to gases other than air that may be externally injected into the passages 152 causing the seal 140 to expand. Examples of materials that increase in volume when absorbing a gas include iron that reacts with oxygen to form iron oxide ($Fe_2O_3$), and zinc oxide that reacts with carbon dioxide to form zinc carbonate. Amines and alcohol amines may also be used in the seal 140 to absorb carbon dioxide.

In yet another example, reduced pressure can be applied to the distribution manifold 130 to create a pressure differential under the drape 132 of sufficient magnitude to cause the expansion of the seal 140. In this example, the seal 140 is formed from a material that expands when a pressure drop exists across the length of the material. In one embodiment, the seal 140 may be a composition comprising a material containing polymer spheres or bubbles (e.g., Expancel® from Akzo Nobel N.V. located at Strawinskylaan 2555, 1077 ZZ Amsterdam, Postbus 75730) that are filled with low boiling point liquids. Upon heating, the polymer softens and the spheres expand so that the seal 140 fills any of the passages 152. Alternatively, the polymer spheres may soften into an elastic state without a significant change in the internal pressure or the corresponding size of the spheres. When a reduced pressure is applied to the seal 140, however, the elastic spheres are subjected to a pressure differential causing them to expand so that the seal 140 fills the passages 152. The pressure differential may be increased further causing the spheres to expand and ultimately rupture releasing their contents, such as gels or adhesives, to fill any of the passages 152 and bind the spheres together to form a tighter seal. Also, the exposed contents may be oxygen sensitive and harden over a period of time to increase the stability of the seal.

The seal 140 and the drape 132 may be applied to the tissue site 101 as a unit, or a care giver can cover the seal 140 with the drape 132 after the seal 140 has been applied. In another embodiment, the care giver may insert all or a portion of the seal 140 under the periphery portion 136 of the drape 132 after the drape 132 has been applied to the tissue site 101. By inserting the seal 140 to the reduced pressure dressing 110 after the reduced pressure dressing 110 has been applied to the tissue site 101, the seal 140 may be used in conjunction with existing wound dressings.

Figure 5:
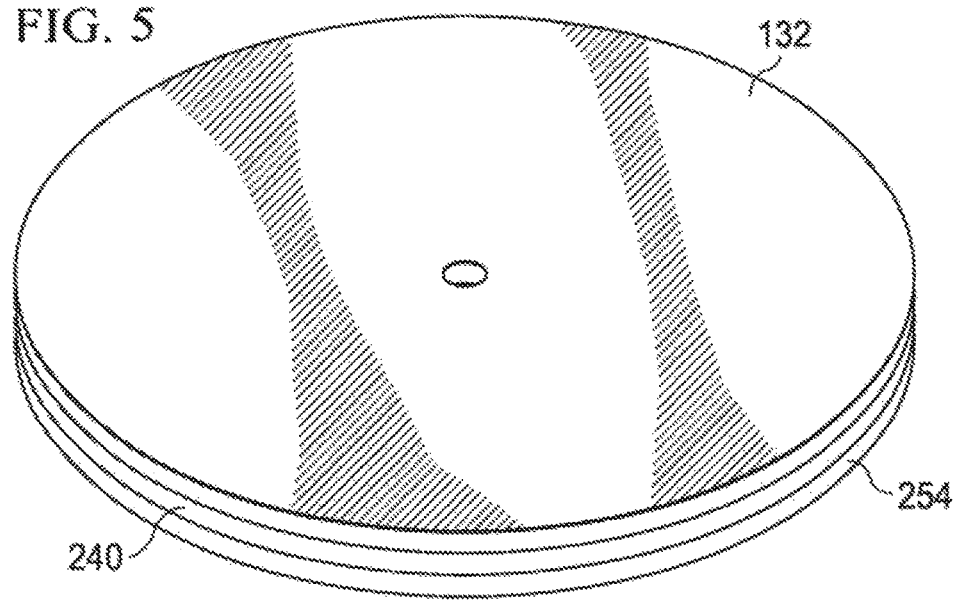
FIG. 5 is a schematic, perspective view of a drape, sealant, and release liner for use with dressing of FIG. 4 according to one illustrative embodiment.
Figure 4:
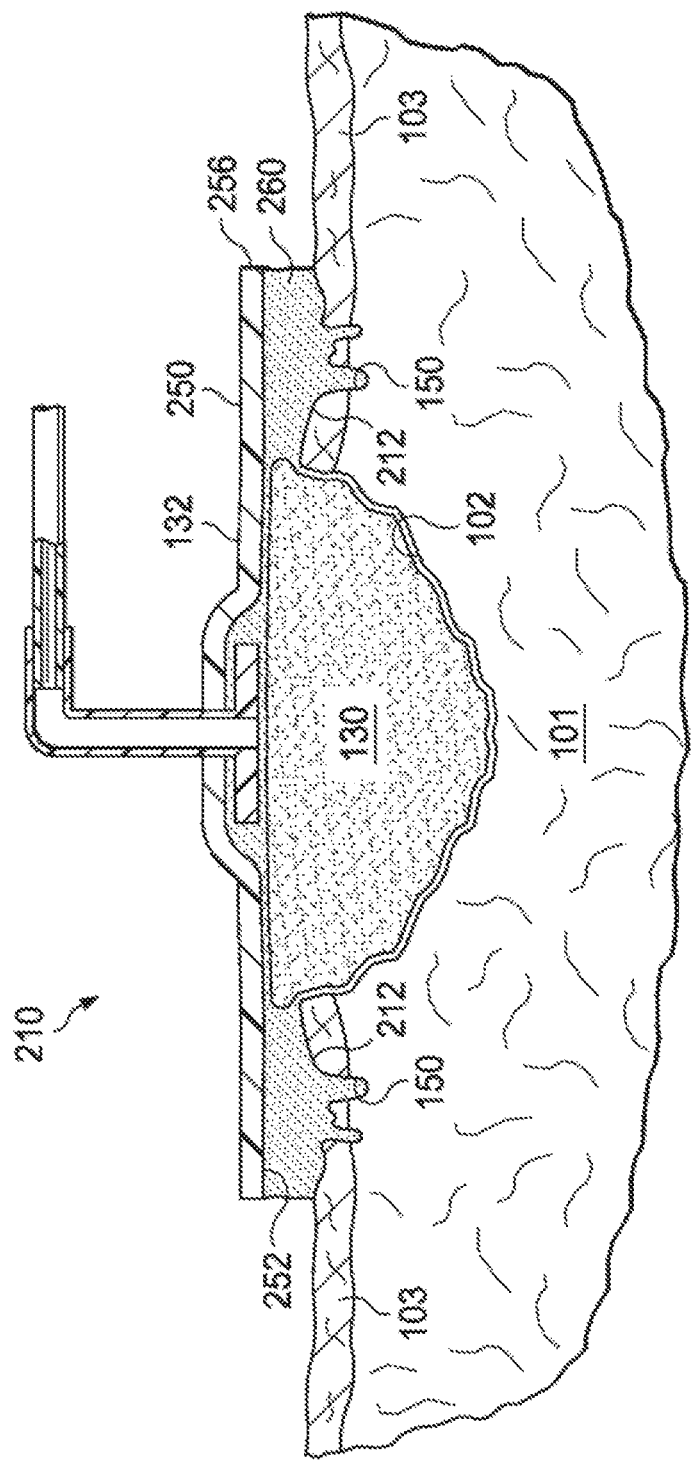
FIG. 4 is a schematic, cross-sectional view of another embodiment of dressing that utilizes a sealant in the reduced-pressure treatment system of FIG. 1.

Referring now to FIGS. 4 and 5, a reduced pressure dressing 210 is shown that includes the drape 132, a seal 240 (as shown in FIG. 5) and the distribution manifold 130. The drape 132 includes a first side 250 and a second, tissue-facing side 252. The seal 240 is different from the seal 140 of FIG. 1 only in shape which covers a substantial portion of the second, tissue-facing side 252 of the drape 132. When the seal 240 transforms to a gelatinous or liquid state to form a sealant 260 as shown in FIG. 4, the sealant 260 covers a larger surface area of the epidermis 103 to plug more of the passages 152 (not shown) resulting from the epidermal discontinuities 150 and drape discontinuities (not shown) as described above. Using a sealant that covers a larger area of contact between the drape 132 and the epidermis 103 may further reduce the number and severity of the passages 152 caused by both discontinuities.

A release liner 254 as shown in FIG. 5 may be utilized to cover a tissue-facing side 212 of the seal 240, prior to application of the reduced pressure dressing 210 to the tissue site 101. The release liner 254 preserves the adhesiveness of the seal 240 prior to the seal's 240 contact with the epidermis 103. The release liner 254 also prevents fluid from contacting the seal 240 prior to application of the reduced pressure dressing 210 to the tissue site 101. The release liner 254 may be formed from any gas or liquid impermeable material to prevent the seal 240 from being contaminated or from transforming to a gelatinous or liquid state before being applied to the tissue site 101. The release liner 254 may also have tabs (not shown) so that a care giver can easily peel the release liner 254 from the seal 240 when desired.

In an alternative embodiment, the seal 240 may be inserted in separate pieces between the drape 132 and the epidermis 103 after the reduced pressure dressing 110 is applied to the tissue site 101. The drape 132 may be applied to the tissue site 101 and held in place by an adhesive (not shown) that may also function as a sealant. The peripheral portion of the drape 132 is free from adhesive to leave a space for inserting pieces of the seal 240 between the drape 132 and the epidermis 103 to plug any of the passages 152 that may be detected after reduced pressure is applied to the wound 102. The separate pieces of the seal 240 do not need to be annular in shape as shown in FIGS. 1 and 4, but rather may be whatever shape necessary to plug the passages 152 that is detected. The separate piece or pieces of seal 240 are inserted under the drape 132 at the desired location and then exposed to any of the stimuli described above, e.g., reduced pressure or fluids, to transform the seal to the sealant 160, 260 as shown in FIGS. 3 and 4, respectively.

Although the present invention and its advantages have been disclosed in the context of certain illustrative, non-limiting embodiments, it should be understood that various changes, substitutions, permutations, and alterations can be made without departing from the scope of the invention as defined by the appended claims.

We claim:

1. A system configured to treat a wound at a tissue site, the system comprising:
    a pressure source configured to supply reduced pressure;
    a manifold configured to be positioned in contact with the wound at the tissue site and configured to be in fluid communication with the pressure source and to provide reduced pressure to the wound at the tissue site;
    a drape having a first side and a second, tissue-facing, side, and wherein the drape is configured to cover the wound at the tissue site and the manifold; and
    a seal in contact with a substantial portion of the second, tissue-facing, side of the drape, wherein the seal is configured to react with a fluid to form a sealant that substantially fills one or more passages between the drape and the tissue site in response to fluid leaking through the one or more passages from outside the drape when the manifold provides reduced pressure to the wound at the tissue site.

2. The system of claim 1, wherein the seal contains an isocyanate material, and wherein the fluid is water vapor contained in the fluid that leaks from outside said drape to contact said seal.

3. The system of claim 1, wherein the seal is a water-sensitive material that liberates gases to form the sealant, and wherein the fluid is water vapor contained in the fluid that leaks from outside said drape to contact said seal.

4. The system of claim 3, wherein the water-sensitive material is a metal hydride or a metal carbide.

5. The system of claim 1, further comprising a fluid supply configured to provide the fluid to the seal.

6. The system of claim 5, wherein the seal is polyurethane, acrylic, or acetate, and wherein the fluid is a solvent.

7. The system of claim 6, wherein the solvent is alcohol, glycol, polyethylene glycol, or glycerine.

8. The system of claim 1, wherein the fluid is a gas configured to react with the seal and expand the seal to form the sealant, and wherein the manifold is configured to draw in the fluid when the tissue site receives reduced pressure.

9. The system of claim 1, wherein the fluid is configured to be pre-applied to the seal.

10. The system of claim 1, wherein the seal comprises one or more polymer spheres configured to expand in response to a pressure differential provided by the pressure source to form the sealant.

11. The system of claim 1, wherein the sealant is configured to at least partially fill the one or more passages formed by a fold in the drape to substantially seal the one or more passages.

12. The system of claim 1, wherein the seal is configured to form an annulus that at least partially surrounds the wound at the tissue site.

13. The system of claim 1, wherein the seal comprises a solid, and wherein the sealant comprises a liquid.

14. The system of claim 1, wherein the fluid comprises air.

15. The system of claim 1, wherein the seal comprises isocyanate, and wherein the seal is configured to react with water vapor in air that is external to the drape to create carbon dioxide gas within the seal.

16. The system of claim 1, wherein the seal comprises a water sensitive polymer that liquefies when exposed to moisture.

17. The system of claim 1, wherein the seal is configured to be disposed between the drape and an area of tissue surrounding the wound at the tissue site.

18. An apparatus configured to treat a wound at a tissue site, the apparatus comprising:
    a manifold configured to be positioned in contact with the wound at the tissue site and configured to be in fluid communication with a pressure source and to provide reduced pressure to the wound at the tissue site;
    a drape having a first side and a second, tissue-facing, side, wherein the second, tissue-facing, side comprises an adhesive, and wherein the drape is configured to cover the wound at the tissue site and the manifold; and
    a seal in contact with a substantial portion of the second, tissue-facing, side of the drape, wherein the seal is configured to react with a fluid to form a sealant that substantially fills one or more passages between the drape and the tissue site in response to fluid leaking through the one or more passages from outside the drape when the manifold provides reduced pressure to the wound at the tissue site.

19. The apparatus of claim 18, wherein the seal contains an isocyanate material reactive with water vapor, and wherein the seal is configured to transform to form the sealant in response to water vapor contained in air when air leaks from outside said drape and contacts the seal.

20. The apparatus of claim 18, wherein the seal is a water-sensitive material that liberates gases to form the sealant in response to water vapor contained in air when air leaks from outside said drape and contacts said seal.

21. The apparatus of claim 20, wherein the water-sensitive material is a metal hydride or a metal carbide.

22. The apparatus of claim 18, wherein the manifold is further configured to provide a fluid to the tissue site, and wherein the seal is configured to transform to form the sealant in response to the fluid contacting the seal.

23. The apparatus of claim 22, wherein the seal is polyurethane, acrylic, or acetate and the fluid is a solvent.

24. The apparatus of claim 23, wherein the solvent is alcohol, glycol, polyethylene glycol, or glycerine.

25. The apparatus of claim 22, wherein the fluid is a gas configured to react with the seal and expand the seal to form the sealant, and wherein the manifold is configured to draw in the fluid when the tissue site receives reduced pressure.

26. The apparatus of claim 18, wherein the seal comprises one or more polymer spheres configured to expand in response to a pressure differential provided by a pressure source to form the sealant.

27. A method for treating a tissue site of a patient, the method comprising:
    applying a dressing to the tissue site, the dressing comprising:

a manifold configured to be:
  positioned in contact with the tissue site, and
  in fluid communication with a pressure source and to communicate reduced pressure to the tissue site;
a drape having a first side and a second, tissue-facing, side, wherein the second, tissue-facing, side comprises an adhesive, and wherein the drape is configured to cover the tissue site and the manifold; and
a seal in contact with a substantial portion of the second, tissue-facing, side of the drape, wherein the seal is configured to react with a fluid to form a sealant that substantially fills one or more passages between the drape and the tissue site in response to fluid leaking through the one or more passages from outside the drape when the manifold provides reduced pressure to the tissue site.

28. The method of claim 27, wherein applying the dressing to the tissue site includes covering the seal with the drape.

29. The method of claim 27, further comprising applying a reduced pressure through the manifold.

30. The method of claim 27, wherein reduced pressure is configured to draw vapor toward the seal to cause expansion of the seal.

31. The method of claim 27, wherein the fluid is configured to contact the seal to cause expansion of the seal.

32. The method of claim 27, further comprising:
applying the fluid to the tissue site prior to applying the dressing to the tissue site.

33. The method of claim 27, further comprising:
applying the fluid to the seal after covering the seal with the drape.

34. The method of claim 27, further comprising:
removing a release liner from the second, tissue-facing, side of the dressing prior to applying the dressing to the tissue site.

* * * * *

UNITED STATES PATENT AND TRADEMARK OFFICE
CERTIFICATE OF CORRECTION

| | | |
|---|---|---|
| PATENT NO. | : 10,792,192 B2 | Page 1 of 1 |
| APPLICATION NO. | : 15/782075 | |
| DATED | : October 6, 2020 | |
| INVENTOR(S) | : Aidan Tout | |

It is certified that error appears in the above-identified patent and that said Letters Patent is hereby corrected as shown below:

On the Title Page

<u>On Page 3, Column 1, Under (Other Publications)</u>
Line 7, delete "Philidelphia," and insert -- Philadelphia, --, therefor.

<u>On Page 3, Column 2, Under (Other Publications)</u>
Line 43, delete "Hypermia" and insert -- Hyperemia --, therefor.

In the Specification

<u>Column 1</u>
Line 8, delete "December" and insert -- Dec. 23, 2013, which --, therefor.

<u>Column 4</u>
Line 60, delete "capralactones." and insert -- caprolactones. --, therefor.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*